United States Patent [19]

Eichhorn et al.

[11] Patent Number: 5,442,087

[45] Date of Patent: Aug. 15, 1995

[54] POLYMERS HAVING N,N-DISUBSTITUTED SULFONAMIDE PENDENT GROUPS AND USE THEREOF

[75] Inventors: Mathias Eichhorn, Niedernhausen; Gerhard Buhr, Koenigstein, both of Germany

[73] Assignee: Hoechst Aktiengesellschaft, Frankfurt am Main, Germany

[21] Appl. No.: 165,148

[22] Filed: Dec. 10, 1993

[30] Foreign Application Priority Data

Dec. 14, 1992 [DE] Germany ............... 42 42 05(

[51] Int. Cl.⁶ ............... C07C 271/12; C07C 271/2 C07C 271/28; C07C 311/(

[52] U.S. Cl. ............................ 560/12; 560/11 560/1·

[58] Field of Search ............ 560/12, 115, 1·

[56] References Cited

U.S. PATENT DOCUMENTS

| | | | |
|---|---|---|---|
| 3,725,356 | 4/1973 | Luders et al. | 260/77.5 C |
| 3,779,778 | 12/1973 | Smith et al. | 96/115 |
| 3,933,894 | 1/1976 | Stephens | 260/4· |
| 3,971,650 | 7/1976 | Schinski | 71/1( |
| 4,101,323 | 7/1978 | Buhr et al. | 96/: |
| 4,247,611 | 1/1981 | Sander et al. | 430/2& |
| 4,248,957 | 2/1981 | Sander et al. | 430/2˙ |
| 4,250,247 | 2/1981 | Sander et al. | 430/270 |
| 4,311,782 | 1/1982 | Buhr et al. | 430/270 |

FOREIGN PATENT DOCUMENTS

| | | |
|---|---|---|
| 0102450 | 3/1984 | European Pat. Off. . |
| 0249139 | 12/1987 | European Pat. Off. . |
| 0366590 | 5/1990 | European Pat. Off. . |
| 0421388 | 4/1991 | European Pat. Off. . |
| 2407668 | 6/1979 | France . |

OTHER PUBLICATIONS

Acta Chemica Scandinavica, Series B–Organic Chemistry and Biochemistry, Bd. 40, Nr. 9, 1986, Copenhagen, DK, pp. 745–750, L. Grehn et al.: "A Simple Method for Tert–Butoxycarbonylation of Amides", Verbindung 21.

Tetrahedron Letters, Bd. 30, Nr. 42, 1989, Oxford, GB, pp. 5709–5712, J. E. Henry et al.: "Mitsunobu Reactions of N–Alkyl and N–Acyl Sulphonamides—An Efficient Route to Protected Amines", Tabelle 2,2. Spalte, Zeilen 1, 2.

(List continued on next page.)

*Primary Examiner*—José G. Dees
*Assistant Examiner*—Barbara S. Frazier
*Attorney, Agent, or Firm*—John M. Genova

[57] ABSTRACT

The invention relates to monomers of the formulae

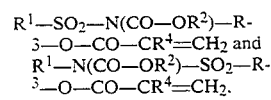

in which $R^1$ is a $(C_1-C_{20})$alkyl, $(C_3-C_{10})$cycloalkyl, $(C_6-C_{14})$aryl or $(C_7-C_{20})$ aralkyl radical, individual methylene groups in the radicals containing alkyl being optionally replaced by heteroatoms, $R^2$ is a $(C_3-C_{11})$alkyl, $(C_3-C_{11})$alkenyl or $(C_7-C_{11})$aralkyl radical, $R^3$ is an unsubstituted or substituted $(C_1-C_6)$alkyl, $(C_3-C_6)$cycloalkyl, $(C_6-C_4)$aryl or $(C_7-C_{20})$aralkyl radical and $R^4$ is a hydrogen atom or a methyl group. It further relates to polymers having at least 5 mol % of units with pendent groups of the formula(e) $—R_3—N(CO—OR^2)—SO_2—R^1$ (I) and/or $—R^3—SO_2—N(CO—OR^2)—R^1$ (II), and to a radiation-sensitive mixture which contains:

a) a compound which under the influence of actinic radiation forms acid, and b) an acid-cleavable compound whose cleavage products in an aqueous-alkaline developer have a higher solubility than the starting compound, in which the acid-cleavable compound is a polymer of the abovementioned type, and to a recording material comprising a support and a radiation-sensitive layer. The mixture according to the invention is particularly suitable for preparing offset printing plates and photoresists.

4 Claims, No Drawings

OTHER PUBLICATIONS

Journal of Medicinal Chemistry, Bd. 35, Nr. 20, Oct. 2, 1992, Washington, D.C., pp. 3641–3647, M. J. C. Lee et al.: "N-Hydroxylated Derivatives of Chlorpropamide and its Analogues as Inhibitors of Aldehyde Dehydrogenase In Vivo", Verbindungen 10B, 11B, 12 B.

Journal of Medicinal Chemistry, Bd. 32, Nr. 6, Jun. 1989, Washington, D.C., pp. 1335–1340, H. T. Nagasawa et al.: "N1–Alkyl Substituted Derivatives of Chlorpropamide as Inhibitors of Aldehyde Dehydrogenase", Verbindung 5.

Synthetic Communications, Bd. 20, Nr. 14, 1990, New York, pp. 2083–2090, I. Atanasova et al.: "α, α, α–Trichlormethylcarbonyl Compounds as Acylating Reagents of Amides", Verbindung 3K.

Chemical Abstracts, vol. 102, No. 13, Apr. 1, 1985, Columbus, Ohio, Abstract No. 113079A, p. 672.

Chemical Abstracts, vol. 93, No. 19, Nov. 10, 1980, Columbus, Ohio; Abstract No. 181032A, p. 191.

Chemical Abstracts, vol. 91, No. 25, Dec. 17, 1979, Columbus, Ohio, Abstract No. 211082v, p. 651.

Chemical Abstracts, vol. 84, No. 25, Jun. 21, 1976, Columbus, Ohio, Abstract No. 175167w, p. 176.

Chemical Abstracts, vol. 88, No. 7, Feb. 13, 1978, Columbus, Ohio, Abstract No. 46376x, p. 179.

Chemical Abstracts, vol. 72, No. 15, Apr. 13, 1970, Columbus, Ohio, Abstract No. 78623m, L. P. Glushko et al.: "Sulphanilides. XXIII. Isopropyl Esters of N–Arylsulphonyl–N–Phenylcarbamic Acids", p. 356.

Chemical Abstracts, vol. 111 (1989); Abstract No. 111.77653h: "Preparation of Sulfonamide Derivatives as Bactericides and Fungicides".

Chemical Abstracts, vol. 114 (1991); Abstract No. 114:185040b: "Preparation of Sulfenylated Carbamates as Insecticides".

POLYMERS HAVING N,N-DISUBSTITUTED SULFONAMIDE PENDENT GROUPS AND USE THEREOF

The invention relates to monomers having N,N-disubstituted sulfonamide groups, polymers which have N,N-disubstituted sulfonamide pendent groups, and to a radiation-sensitive mixture which contains:

a) a compound which under the influence of actinic radiation forms acid;
b) an acid-cleavable compound whose cleavage products in an aqueous-alkaline developer have a higher solubility than the starting compound; and
c) a polymeric binder which is insoluble in water but is soluble or at least swellable in aqueous alkaline solutions.

It is particularly suitable for a recording material comprising a base and a radiation-sensitive layer for preparing offset printing plates and photoresists.

Positive radiation-sensitive recording layers, i.e. layers whose solubility is greater in the irradiated zones than in the non-irradiated ones, are known. As the photosensitive component in such layers, ortho-naphthoquinone diazides in particular have gained general acceptance. The photosensitivity of these layers is usually unsatisfactory, however.

The so-called "chemically enhanced" mixtures in comparison show a higher photosensitivity, as the quantum yield is greater than 1. Positive "chemically enhanced" mixtures as a rule contain an acid-forming and an acid-cleavable component, whose cleavage products in aqueous alkaline developers have a greater solubility than the initial compound.

The acid-cleavable compounds used hitherto were monomeric and polymeric acetals and O,N- acetals which as the hydroxyl or amino component contain aromatic compounds (U.S. Pat. No. 3,779,778) and orthoesters and amide acetals (DE-B 26 10 842).

Radiation-sensitive positive mixtures are also obtained when employing polymeric orthoesters (EP-B 0 022 571), polymeric aliphatic acetals (DE-A 27 18 254), enol ethers (EP-B 0 006 627) and N-acyliminocarbonates (EP-B 0 006 626). Mixtures of this type, in order to initiate the cleavage reaction, require not only the photochemically generated acid, but also water, which leads to problems in practical applications. Furthermore, many of these compounds are not readily accessible.

A positive radiation-sensitive mixture which contains a compound which upon irradiation produces acid, and also contains a polymer having pendent, acid-labile t-butoxycarbonyl or t-butoxycarbonyloxy groups, is described in EP-A 0 102 450 and in EP-A 0 366 590. A similar mixture, which, however, instead of said polymers contains low-molecular weight compounds having acid-labile groups is disclosed in EP-A 0 249 139. Disclosed as acid-labile groups in the low-molecular weight compounds which generally have a molecular weight of less than 1000 are, in particular, t-butoxy, t-butoxycarbonyl, t-butoxycarbonyloxy, 1-methyl-1-phenylethoxycarbonyl and trimethylsilanyloxy groups. While such systems do not require water for initiating the cleavage reaction, they are not devoid of drawbacks either; for example, they show relatively high "dark ablation", i.e. the solubility of the radiation-sensitive layer in a developer is relatively high even in the unexposed zones, which results in poor differentiation between exposed and unexposed zones.

The object of the invention is to develop acid-cleavable compounds which can be produced simply and inexpensively and which are particularly suitable for a positive "chemically enhanced" mixture which has a high sensitivity with respect to actinic radiation, especially the radiation emitted by excimer lasers and high-pressure mercury lamps.

This object is achieved according to the invention by providing monomers having N,N-disubstituted sulfonamide groups of the formulae $—R^3—N(CO—OR^2)—SO_2—R^1$(I) or $—R^3—SO_2—N(CO—OR^2)—R^1$(II), and polymers having at least 5 mol % of units with pendent groups of the formula(e) I and/or II, in which $R^1$ is a $(C_1–C_{20})$alkyl, $(C_3–C_{10})$cycloalkyl, $(C_6–C_{14})$ aryl or $(C_7–C_{20})$aralkyl radical, individual methylene groups in the radicals containing alkyl being optionally replaced by heteroatoms, $R^2$ is a $(C_3–C_{11})$alkyl, $(C_3–C_{11})$alkenyl or $(C_7–C_{11})$aralkyl radical, $R^3$ is a $(C_1–C_{12})$-alkylene, $(C_3–C_{12})$cycloalkylene, $(C_6–C_{15})$arylene or $(C_8–C_{20})$arylenedialkyl radical.

$R^2$ is preferably a $(C_3–C_6)$alkyl radical, particularly preferably isopropyl, sec-butyl or t-butyl radical. $R^3$ is preferably an unsubstituted or substituted $(C_1–C_6)$alkylene, $(C_3–C_6)$cycloalkylene, $(C_6–C_{14})$arylene or $(C_8–C_{20})$arylenedialkyl radical.

As the examples show, the polymers preferably contain from about 10 to about 90 mol %, particularly preferably from about 20 to about 80 mol % of units with groups of the formula I or II. Copolymers are therefore generally preferred to homopolymers. The polymers generally have a molecular weight in the range from about 2,000 to about 100,000, preferably from about 5,000 to about 50,000.

Suitable comonomers are, in principle, all the polymerizable compounds without acid-clearable groups. "Non-acid clearable" in this context means that the groups are not cleaved by the acid generated in the mixture according to the invention. Such comonomers are, for example, acrylic acid, methacrylic acid, $(C_1–C_{10})$alkyl acrylates and methacrylates, $(C_6–C_{10})$aryl acrylates and methacrylates (especially phenyl acrylate, phenyl methacrylate and pyrocatechol monomethacrylate), acrylamide, methacrylamide, optionally substituted N-$(C_1–C_{10})$alkylacrylamide and -methacrylamide (especially N-(2-hydroxyethyl)-acrylamide and -methacrylamide), N,N-di$(C_1–C_{10})$alkylacrylamide, N-phenylacrylamide and -methacrylamide, N,N-diphenylacrylamide and -methacrylamide, N-$(C_1–C_{10})$alkyl-N-$(C_6–C_{10})$arylacrylamide (especially N-phenyl-N-methylacrylamide and -methacrylamide), N-phthalimidomethyl-methacrylamide, allyl compounds such as allyl esters and allyl oxyethanol, vinyl compounds such as vinyl ethers and vinyl esters, vinyl aromatics such as styrene, alkylstyrene, alkoxystyrene, hydroxystyrene, alkyl-hydroxystyrene, acetoxystyrene, α-methylstyrene, α-methyl-hydroxystyrene, and finally also acrylonitrile and methacrylonitrile. Less preferred, but expedient under certain circumstances, is the use of comonomers having acid-cleavable groups.

Preferred monomers having N,N-disubstituted sulfonamide groups of the formula I are $R^1$ —$SO_2$—$N(CO—OR^2)$—$R^3$—$O$—$CO$—$CR^4$=$CH_2$, preferred monomers having groups of the formula II are $R^1$—$N(CO—OR^2)$—$SO_2$—$R^3$—$O$—$CO$—$CR^4$=$CH_2$, where $R^4$ is a hydrogen atom or a methyl group. The preferred monomers are therefore acrylates or methacrylates.

The monomers with N,N-disubstituted sulfonamide groups can be prepared from the corresponding compounds having N-monosubstituted sulfonamide groups, by reacting these, in the presence of a catalytic amount of an organic base such as 4-dimethylaminopyridine, with activated carbonic acid esters which contain the group —$OR^2$ as the alcohol component.

N-Monosubstituted sulfonamides can be prepared according to methods known to those skilled in the art from sulfonic acids and primary amines. The preparation of the monomers having groups of the formula II generally employs monoamines. Preferred monoamines are straight-chain or branched alkylamines having from 1 to 12, particularly preferably from 1 to 6, carbon atoms, such as methylamine, ethylamine, propylamine, isopropylamine, butylamine, sec-butylamine, isobutylamine, t-butylamine, pentylamine, 1-methylbutylamine, 2-methylbutylamine and hexylamine. Also preferred are cycloalkylamines having from 3 to 12, particularly preferably from 5 to 8, carbon atoms, such as cyclopentylamine, cyclohexylamine, cycloheptylamine and cyclooctylamine. Of the aromatic monoamines, those having from 6 to 15 carbon atoms are preferred, and their aromatic part can be substituted, especially with halogen atoms, alkyl or alkoxy groups. Examples of preferred aromatic amines are aniline, 4-methylaniline, 4-ethylaniline, 4-methoxyaniline, 3-methoxyaniline, 4-ethoxyaniline, 4-phenoxyaniline, naphthylamine, biphenylamine, 1- and 2-aminoanthracene and 9-aminophenanthrene. Among the aralkylamines, those having from 7 to 20 carbon atoms are preferred. These may be substituted in the same way as the aromatic amines. Relevant examples are benzylamine, 4-methoxybenzylamine, 2,2- and 3,3-diphenylpropylamine.

The preparation of the monomers having groups of the formula I employs primary amines having a polymerizable olefinically unsaturated group or a functional group which establishes the bond to such a polymerizable group. Particularly suitable for preparing the abovementioned acrylates and methacrylates are hydroxyamines such as ethanolamine. By reacting the hydroxy group with, for example, methacrylic anhydride it is then possible to introduce the polymerizable double bond.

The same comments apply to the sulfonic acids used for preparing the monomers as to the amines. Sulfonic acids preferred for the preparation of the monomers having groups of the formula I are methanesulfonic acid, trifluoromethanesulfonic acid, ethanesulfonic acid, propanesulfonic acid, perfluoropropanesulfonic acid, perfluorobutanesulfonic acid, hexanesulfonic acid, perfluorooctanesulfonic acid, benzenesulfonic acid, pentafluorobenzenesulfonic acid, para-toluenesulfonic acid and naphthalenesulfonic acid. The preparation of the monomers having groups of the formula II accordingly employs sulfonic acids which have been functionalized in the same way as the amines for preparing the monomers having groups of the formula I. An example of a functionalized sulfonic acid is 4-hydroxybenzenesulfonic acid.

The sulfonic acids are generally not employed as such in the reaction, but in a more reactive, so-called "activated" form. These include, in particular, the sulfonyl halides, especially the sulfonyl chlorides.

So-called "activated carbonic acid esters" are those which can effect acylation of the N-monosubstituted sulfonamides with —CO—$OR^2$. These are, in particular, dialkyldicarbonates (=pyrocarbonic acid dialkyl esters). Particularly preferred is di-t-butyl dicarbonate (=$O[CO_2—C(CH_3)_3]_2$).

The reaction of the N-monosubstituted sulfonamides with the activated carbonic acid esters is preferably carried out in a solvent which, under the reaction conditions, does not enter into any irreversible reactions with the other components of the reaction mixture, in the presence of from about 0.01 to about 10 mol %, preferably from about 0.05 to about 2 mol %, in each case based on the molar amount of N-monosubstituted sulfonamide, of an organic base. Said base is preferably a tertiary amine, e.g. dialkylaminopyridine. Suitable solvents are, in particular, tetrahydrofuran, ethyl acetate, diethyl ether, butanone (=methyl ethyl ketone). It was found to be expedient to introduce the N-monosubstituted sulfonamide and the organic base in dissolved form as an initial charge and to slowly add to this mixture the activated carbonic acid ester. The reaction is generally carried out at a temperature of from about 0° to about 80° C., preferably from about 10° to about 50° C. The reaction product can then be isolated with sufficient purity by pouring the reaction mixture into water, filtering the precipitate and drying, or simply by stripping off the volatile constituents under reduced pressure. If required, further purification can be carried out by recrystallization, reprecipitation, distillation or by a preparative chromatographic method.

According to the invention there is further proposed a radiation-sensitive mixture which contains:
a) a compound which under the influence of actinic radiation forms acid; and
b) an acid-cleavable compound whose cleavage products in an aqueous-alkaline developer have a higher solubility than the starting compound; wherein the acid-cleavable compound b) is a polymer having at least 5 mol % of units having N,N-disubstituted sulfonamide pendent groups of the formula I or II.

Suitable as compounds a) which under the influence of actinic radiation form preferably strong acids are, inter alia, and in particular, diazonium, phosphonium, sulfonium and iodonium salts, halogen compounds, o-quinone diazidesulfochlorides, esters and amides and also organometallic/organohalogen combinations. Said diazonium, phosphonium, sulfonium and iodonium compounds are, as a rule, employed in the form of their salts soluble in organic solvents, particularly in the form of the sulfonates, especially trifluoromethanesulfonates, of tetrafluoroborates, hexafluorophosphates, hexafluoroantimonates or hexafluoroarsenates. However, it is also possible to use halides, esters and amides of 1,2-naphthoquinone-2-diazide sulfonic acids. The acidity of the indene carboxylic acids produced upon irradiation of o-naphthoquinone diazides is, however, usually only barely adequate for sufficient imagewise differentiation. Preference is therefore given among this group to the 1,2-naphthoquinone-2-diazide-4-sulfonyl chloride, upon whose irradiation three acid functions are formed, so that a relatively large enhancement factor obtains. Finally, suitable acid formers also include organic halogen compounds, for example those having more than one halogen atom on a carbon atom or an aromatic ring. The spectral sensitivity of said halogen-containing compounds can be modified and increased by sensitizers known per se. Examples of particularly suitable acid formers are 1,2-naphthoquinone-2-diazide-4-sulfonyl chloride; 4-dipropylaminobenzenediazonium tetrafluoroborate, hexafluorophosphate and trifluoromethanesulfonate; 2,5-diethoxy-4-p-tolylmercaptobenzenediazonium tetrafluoroborate, hexafluorophosphate and trifluoromethanesulfonate; 4-anilinobenzenediazonium sulfate and 4-diethylaminobenzenediazonium trifluoromethanesulfonate, as well as the compounds mentioned in the examples. It is also possible to use 4-methyl-6-trichloromethyl-2-pyrone; 4-(3,4,5-trimethoxystyryl)-6-trichloromethyl-2-pyrone; 4-(4-methoxystyryl)-6-(3,3,3-trichloropropenyl)-2-pyrone; 2-trichloromethylbenzimidazole; 2-tribromomethylquinolin-4-one; 2,4-dimethyl-1-tribromoacetylbenzene; 3-nitro-1-tribromoacetylbenzene; 4-dibromoacetylbenzoic acid; 1,4-bis-dibromomethylbenzene; substituted 4,6-bis-trichloromethyl-s-triazines such as 2-(6-methoxynaphthalen-2-yl)-, 2-(naphthalen-1-yl)-, 2-(naphthalen-2-yl)-, 2-[4-(2ethoxyethyl)-naphthalen-1-yl]-, 2-benzopyran-3-yl, 2-phenanthren-9-yl and 2-(4-methoxyanthracen-1-yl)-4,6-bis-trichloromethyl-s-triazine and tris-dibromomethyl-s-triazine.

The proportion of the acid-forming compound(s) a) in the mixture varies according to the composition of the mixture. Favorable results are obtained with from about 0.1 to about 20% by weight, preferably from about 0.2 to about 10% by weight, in each case based on the total weight of the solids in the mixture. Particularly in the case of copying layers having a thickness of more than 10 μm it is advisable to use relatively small amounts of acid former.

The proportion of the acid-cleavable polymers b) in general is from about 30 to about 98% by weight, preferably from about 50 to about 95% by weight, in each case based on the total weight of the solids in the mixture.

In addition to the acid-cleavable compounds according to the invention, others may be present in the mixture. These are, in particular, polymers having t-butoxycarbonyl groups. Mixtures having such further acid-cleavable compounds are in general not preferred, however.

If required, the mixture may in addition contain polymeric organic binders. Particularly suitable polymeric binders are phenol resins, especially cresol-formaldehyde novolaks (melting range 105°–120° C. according to DIN 53181) and phenol-formaldehyde novolaks (melting point 110°–120° C. according to DIN 53181).

The type and proportion of the binder depend on the application purpose. Preference is given to a proportion of t from about 5 to about 70% by weight, particularly preferably from about 20 to about 50% by weight, in each case based on the total weight of the solids in the mixture.

Binders, whose alkali solubility is increased by the action of acid, can likewise be used in the mixture according to the invention. Such binders may be, e.g., polyhydroxystyrenes whose phenolic OH groups are furnished with acid-labile groups which reduce alkali solubility. The compounds according to the invention bring about a distinct reduction of the dark ablation without adversely affecting the photosensitivity of the mixture.

Other alkali-soluble resins such as copolymers from methacrylic acid and methyl methacrylate, vinyl acetate and crotonic acid, as well as maleic anhydride and styrene are likewise suitable as binders.

In addition, numerous other resins can be used at the same time, preferably vinyl polymers such as poly(vinyl acetates), polyacrylates, poly(vinyl ethers) and poly(vinylpyrrolidones) which in turn may be modified by comonomers. The most advantageous proportion of these resins depends on the application requirements and the effect on the development conditions. In general, it is not more than about 50% by weight, based on the total weight of the solids in the mixture.

In order to meet special requirements such as flexibility, adhesion or gloss, the radiation-sensitive mixture may additionally contain substances such as polyglycols, cellulose derivatives such as ethyl cellulose, wetting agents, dyes and finely dispersed pigments. Dyes which have been found to be particularly useful are the triphenylmethane dyes, especially in the form of their carbinol bases. The most advantageous quantitative ratios of the components can easily be found by experiments for each specific case.

The present invention finally also relates to a recording material comprising a base and a radiation-sensitive layer comprising the mixture according to the invention. The recording material is usually prepared by coating the base with a solution of the mixture.

Suitable solvents for the radiation-sensitive mixture according to the invention are ketones such as methyl ethyl ketone, chlorinated hydrocarbons such as trichloroethylene and 1,1,1-trichloroethane, alcohols such as n-propanol, ethers such as tetrahydrofuran, glycol ethers such as ethylene glycol monoethyl ether, and esters such as butyl acetate. It is also possible to use mixtures which, moreover, for special purposes may additionally contain solvents such as acetonitrile, dioxane or dimethylformamide. In principle, all solvents can be used which do not react irreversibly with the layer components. They should, however, be selected with regard to the coating process intended, the layer thickness and the drying appliance. Thin layers up to approximately 5 μm in experimental amounts are preferably applied by spin-coating. Layer thicknesses of more than 60 μm can be achieved with solutions of up to about 40% solids content by a single application to the spinning disc or using a doctor knife. Bilateral coating is preferably effected by dip-coating, rapid surface drying being advantageous and being achieved by employing low-boiling solvents. Strip-shaped base materials can be coated by spraying the coating solution using sheet dies or by application using rollers; individual plates, such as zinc and multimetal plates, can be coated by curtain coating.

Compared to other positive layers, especially those based on o-naphthoquinone diazide, it is also possible to produce thicker layers, as the photosensitivity of the mixtures according to the invention varies comparatively little with thickness. Exposure and processing of layers having a thickness of 100 μm and more is possible.

Preferred bases for layers having a thickness of more than 10 μm are plastic sheets which then serve as temporary bases for transfer layers. For this purpose and for color sheets, polyester sheets are preferred, e.g. from polyethylene terephthalate. Polyolefin sheets such as polypropylene are likewise suitable, however. If layer thicknesses are less than 10 μm, the film bases employed are usually metals. Offset printing plates can be manufactured by employing mechanically or electrochemically roughened and optionally anodized aluminum, which may be pretreated chemically (e.g. with polyvinylphosphonic acid, silicates or phosphates). Also suitable are multi-metal plates having Cu/Cr or brass/Cr as the uppermost layer. To prepare relief printing plates, the layers produced from the mixture according to the invention can be applied to zinc or magnesium plates or their commercial microcrystalline alloys for powderless etching, also to etchable plastics such as polyoxymethylene. For the purpose of rotogravure or halftone formes these layers are suitable owing to their good adhesion and etch resistance on copper or nickel surfaces. Similarly, they can be used as photoresists and in chemical milling.

Finally, coating can be effected directly or by dry layer transfer from the temporary base to printed-circuit board materials comprising insulating plates coated with copper on one side or both sides, onto glass or ceramic materials which may, if appropriate, have been pretreated to promote adhesion, and, inter alia, to silicon wafers on whose surface there may be, if appropriate, a nitride or oxide layer. In addition, it is possible to coat wood, textiles and surfaces of many materials which are preferably illustrated by a projection and are resistant to the influence of alkaline developers.

The coating can be dried with the usual equipment, employing the usual conditions. It withstands temperatures around 100° C., on a short-term basis even as high as 120° C., without a loss in radiation sensitivity being observed subsequently.

Irradiation can be carried out employing the usual radiation sources, such as tubular lamps, pulsed xenon discharge lamps, metal halide-doped high-pressure mercury vapor lamps and carbon arc lamps. In addition, it is possible to irradiate in conventional projection and enlargement equipment under the light of metal filament lamps, or contact exposure using ordinary light bulbs is possible. Irradiation can alternately be effected with the coherent light of a laser. Suitable for this purpose are high-power short-wavelength lasers, for example argon ion lasers, krypton ion lasers, dye lasers, helium-cadmium lasers and excimer lasers emitting between 193 and 633 nm. The laser is usually passed over the recording layer under computer control in a raster- or stroke-like manner and in the process irradiates the latter image wise.

Irradiation with electron beams forms a further illustration possibility. Electron beams are able to decompose thoroughly and then crosslink the mixture according to the invention, like many other organic materials, so that a negative image is produced if the non-irradiated regions are removed by solvents or exposure without a pattern and development. If the intensity of the electron beam is lower, and/or the writing speed thereof is higher, the electron beam, in contrast, has a differentiating effect in the direction of higher solubility, i.e. the irradiated layer portions can be removed by the developer. The most favorable conditions to be chosen are easily determined by experiments.

The layer, after imagewise exposure or irradiation, can be removed, after thermal secondary treatment if required, using virtually the same developers as for commercially available naphthoquinone diazide layers and photoresists, and the novel layers, as far as their copying conditions are concerned, can be advantageously tailored to the conventional aids such as developers and programmed spray development equipment. The aqueous developer solutions may contain, e.g., alkali metal phosphates, silicates or hydroxides and also wetting agents as well as minor proportions of organic solvents. In certain cases it is possible to use, instead of the aqueous alkaline developers, organic solvents or mixtures of organic solvents with water as the developer. The preferred developers, however, are aqueous alkaline solutions.

The most advantageous developer can be determined by experiments with the layer in a particular case. If required, development can be assisted mechanically. So as to increase the robustness during printing and the resistance against leaching agents, correcting agents and inks curable by UV light, the developed plates may be heated to elevated temperatures for a short time.

Hereinafter, examples are given of the preferred monomers according to the invention having N,N-disubstituted sulfonamide groups, of polymers produced therewith and of preferred photosensitive mixtures produced with the aid of the polymers, without restricting the invention to these. In the examples, ppw represents parts by weight.

Preparation of monomers

I. N-t-butoxycarbonyl-N-(2-methacryloyloxyethyl)-p-toluenesulfonamide a) 100 g of p-toluenesulfonyl chloride are slowly added over 1.5 hour to 80 ml of ethanolamine while cooling with ice. The reaction mixture is then heated to 120° C. and is then held at this temperature for 3 hours. After cooling to 70° C., a mixture of 60 ml of concentration HCl and 300 ml of water is added. After stirring for 10 min, 300 ml of methylene chloride are added, and the organic phase is separated and dried with $MgSO_4$. After stripping off the solvent on the rotary evaporator, 111.6 g of a slightly yellowish solid [N-(2-hydroxyethyl)-p-toluenesulfonamide] are obtained. The product can be used in the next step without further purification.

b) 6.8 ml of methacrylic anhydride and 6.3 ml of triethylamine are added dropwise, while cooling with ice, to a solution of 8.9 g of N-(2-hydroxyethyl)-p-toluenesulfonamide in 50 ml of butanone. The reaction mixture is allowed to reach room temperature and is then refluxed for another 4 hours. After cooling, ethylacetate is added, the mixture is washed with water, the organic phase is separated and dried with magnesium sulfate. After stripping off the solvent on the rotary evaporator, there remain 11.2 g of an oil [N-(2-methacryloyloxyethyl)-p-toluenesulfonamide]. The oily product can be used directly in the next step.

c) 11.8 g of the crude N-(2-methacryloyloxyethyl)-p-toluenesulfonamide obtained in the previous step are dissolved in 50 ml of ethyl acetate. While stirring, 10 mg of 4-dimethylaminopyridine are first added at room temperature, followed by 9.2 g of di-t-butyl dicarbonate (pyrocarbonic acid di-t-butyl ester). When the reaction has finished, the reaction mixture is washed with a 10% aqueous NaOH solution. The organic phase is then separated and dried with $MgSO_4$. After stripping off the solvent on the rotary evaporator, there remain 14 g of a slightly colored oil (N-t-butoxycarbonyl-N-(2-methacryloyloxyethyl)-p-toluenesulfonamide].

$^1$H-NMR spectrum (60 MHz, $CDCl_3$ as the solvent; chemical shift in ppm on the δ scale: number of protons in brackets): 1.3 [9H], 1.95 [3H], 2.45 [3H], 4.0–4.6 [4H], 5.55 [1H], 6.15 [1H], 7.15–7.4 [2 H], 7.65–7.95 [2H].

II. N-t-butoxycarbonyl-4-methacryloyloxy-N-phenyl-benzenesulfonamide a) 200 g of the Na salt of 4-hydroxybenzenesulfonic acid are dissolved in 500 ml of 2N aqueous NaOH, followed by dilution with 200 ml of water and dropwise addition, with stirring at room temperature, of 120 g of ethylchloroformate. The mixture is left to stand overnight and the precipitate formed (87 g) is filtered off with suction. Stripping off of the solvent under reduced pressure and recrystallization from ethanol gives a further 129 g of 4-ethoxycarbonyloxybenzenesulfonic acid Na salt (white solid). The total yield is 216 g (92% of theory).

b) 95 g of the well-dried 4-ethoxycarbonyloxybenzenesulfonic acid Na salt obtained under a) are well mixed with 95 g of PCl₅, the reaction mixture liquefying in the process and heating up. It is heated for a further 2 hours in an oil bath (bath temperature 115° C.), left to stand overnight at room temperature, poured onto ice, and the sulfonyl chloride is filtered off with suction. After washing with large amounts of cold H₂O and drying under reduced pressure, 88 g (94% of theory) of 4-ethoxycarbonyloxybenzenesulfonyl chloride are obtained (white solid with a melting point (mp.) of 71°–72° C.).

c) 340 ml of aniline are admixed, with stirring and a little at a time, with 84 g of the 4-ethoxycarbonyloxybenzenesulfonyl chloride prepared under b). The mixture is heated for 4 hours at 55° C., allowed to cool down to room temperature and poured into 1.7 l of half-concentrated hydrochloric acid. After standing overnight, the aqueous phase is decanted. For the purpose of complete removal of the protective group, the residue is taken up in 1.7 l of 2N aqueous NaOH, any undissolved material is separated, and the product is precipitated by acidifying with HCl. After filtering off with suction, washing with H₂O and drying, 54.5 g (70% of theory) of 4-hydroxybenzenesulfanilide (white solid, mp.: 140° C.) are obtained.

d) 50 g of the 4-hydroxybenzenesulfanilide prepared under c) are dissolved in 300 ml of acetone, 35.6 g of methacrylic anhydride are added, and 22.3 g of triethylamine are added dropwise while cooling and stirring, in such a way that the temperature does not rise above 10° C. The reaction solution is allowed to reach room temperature and is added dropwise, while stirring vigorously, into 3 l of H₂O. After filtering off with suction and drying, 61 g (96%) of 4-methacryloyloxybenzenesulfanilide (white solid, mp.: 102°–103° C.) are obtained.

e) 50 g of the 4-methacryloyloxybenzenesulfanilide prepared under d) are dissolved in 300 ml of acetone, 1 g of 4-dimethylaminopyridine is added, and a solution of 38 g of di-t-butyldicarbonate in 100 ml of acetone is added dropwise with stirring. Stirring is continued for 4 hours at room temperature and precipitation carried out in H₂O. After filtering off with suction and drying, 59 g (90%) of N-t-butoxycarbonyl-4-methacryloyloxy-N-phenylbenzenesulfonamide (white solid, mp.: 112°–114° C.) are obtained.

NMR spectrum (60 MHz, CDCl₃): 1.3 ppm (9H), 2.1 (3H); 5.8 (1H), 6.4 (1 H); 7.2–7.6 (7H); 8.0–8.2 (2H).

Examples 1 to 20

Homopolymerization of I and II, and copolymerization using various comonomers, such as pyrocatechol monomethacrylate (PMA) or styrene is carried out according to methods known from the literature. Table 1 contains a selection of polymers which were synthesized employing I and II (amounts specified in mol percent).

TABLE 1

| Example | I  | II | PMA | Styrene |
|---------|----|----|-----|---------|
| 1       | 10 | —  | 90  | —       |
| 2       | 30 | —  | 70  | —       |

TABLE 1-continued

| Example | I  | II | PMA | Styrene |
|---------|----|----|-----|---------|
| 3       | 50 | —  | 50  | —       |
| 4       | 70 | —  | 30  | —       |
| 5       | 90 | —  | 10  | —       |
| 6       | 10 | —  | 85  | 5       |
| 7       | 15 | —  | 80  | 5       |
| 8       | 15 | —  | 75  | 10      |
| 9       | 10 | —  | 80  | 10      |
| 10      | 20 | —  | 75  | 5       |
| 11      | 20 | —  | 70  | 10      |
| 12      | —  | 10 | 90  | —       |
| 13      | —  | 10 | 85  | 5       |
| 14      | —  | 10 | 80  | 10      |
| 15      | —  | 15 | 85  | —       |
| 16      | —  | 15 | 80  | 5       |
| 17      | —  | 15 | 75  | 10      |
| 18      | —  | 20 | 80  | —       |
| 19      | —  | 20 | 75  | 5       |
| 20      | —  | 20 | 70  | 10      |

Examples 21 to 26

These examples show the preparation and processing of recording materials according to the invention.

A plate of electrochemically activated and anodized aluminum is spin-coated with a solution comprising:

9.00 ppw of binder according to Table 1, 0.50 ppw of 4-p-tolylmercapto-2,5-diethoxybenzenediazonium hexafluorophosphate, 0.08 ppw of crystal violet base and 175 ppw of methyl ethyl ketone and heated at 100° C. in a drying oven, resulting in a layer thickness of 1.9 μm. The plate is exposed under a 5 kW metal halide lamp at a distance of 110 cm through a halftone step wedge having 13 steps with a density gradation of 0.15, is then heated for 1 min at 100° C. and developed for 30 s in an aqueous alkaline developer having the composition:

5.5 ppw of sodium metasilicate -9 H₂O 3.4 ppw of trisodium phosphate -12 H₂O 0.4 ppw of monosodiumphosphate anhydrous and 90.7 ppw of deionized water.

In all cases, a positive image of the photographic master is obtained. Table 2 indicates at what exposure time step 4 of the halftone wedge is reproduced as completely open on the plate.

TABLE 2

| Example | Polymer according to Table 1 | Exposure time (s) |
|---------|------------------------------|-------------------|
| 21      | 8                            | 30                |
| 22      | 10                           | 30                |
| 23      | 11                           | 35                |
| 24      | 18                           | 20                |
| 25      | 15                           | 18                |
| 26      | 17                           | 30                |
| Comparison* | —                        | 75                |

*Standard positive printing plate ®Ozasol P61 (Hoechst AG)

Example 27

This example shows the suitability of the polymers containing N,N-disubstituted sulfonamide groups for use in positive offset printing plates.

A plate of electrochemically activated and anodized aluminum is spin-coated with a solution comprising:

9.00 ppw of terpolymer according to Table 1, No. 19, 0.50 ppw of 4-p-tolylmercapto-2,5-diethoxybenzenediazonium hexafluorophosphate, 0.08 ppw of crystal violet base and
175 ppw of methyl ethyl ketone and heated at 100° C. in a drying oven, resulting in a layer thickness of 1.9 μm. The plate is exposed for 20 seconds under a 5 kW metal halide lamp at a distance of 110 cm through a halftone step wedge having 13 steps with a density gradation of 0.15, is then heated for 1 min at 100° C and developed for 30 seconds in an aqueous alkaline developer (composition see Examples 21–26). The positive printing form thus obtained produces more than 170,000 good-quality prints on an offset printing machine.

We claim:

1. Compounds of the formuale $R^1-SO_2-N(CO-OR^2)-R^3-O-CO-CR^4=CH_2$ or $R^1-N(CO-OR^2)-SO_2-R^3-O-CO-CR^4=CH_2$, in which:

$R^1$ is a $(C_1-C_2)$alkyl, $(C_3-C_{10})$cycloalkyl, $(C_6-C_{14})$aryl or $(C_7-C_{20})$aralkyl radical, individual methylene groups in the radicals containing alkyl being optionally replaced by heteroatoms;

$R^2$ is a $(C_3-C_{11})$alkyl, $(C_3-C_{11})$alkenyl or $(C_7-C_{11})$aralkyl radical;

$R^3$ is a $(C_3-C_{12})$alkylene, $(C_3-C_{12})$cycloalkylene, $(C_6-C_{15})$arylene or $(C_8-C_{20})$arylenedialkyl radical; and $R^4$ is a hydrogen atom or a methyl group.

2. The compound as claimed in claim 1, wherein $R^2$ is a $(C_3-C_6)$alkyl radical.

3. The compound as claimed in claim 2, wherein $R^2$ is an isopropyl, sec-butyl or tert-butyl radical.

4. The compound as claimed in claim 1, wherein $R^3$ is a $(C_1-C_6)$alkylene, $(C_3-C_6)$cycloalkylene, $(C_6-C_4)$arylene or $(C_8-C_{20})$arylenedialkyl radical.

* * * * *

UNITED STATES PATENT AND TRADEMARK OFFICE
CERTIFICATE OF CORRECTION

PATENT NO.   : 5,442,087
DATED        : August 15, 1995
INVENTOR(S)  : Eichhorn et al.

It is certified that error appears in the above-indentified patent and that said Letters Patent is hereby corrected as shown below:

Abstract, line 7 in the line beginning ")cycloalkyl,", "$(C_6-C_4)$aryl" should
be -- $(C_6-C_{14})$ aryl --.
lines 15 & 16   in the line beginning "pendent groups",
"$-R_3-N(CO-OR^2)-SO_2-R^1(I)$" should be -- $-R^3-N(CO-OR^2)-SO_2-R^1(I)$ --.
Column 2, line 39, "acid-clearable" should be -- acid-cleavable --.
Column 2, line 40, "clearable" should be -- cleavable --.
Claim 1, column 12, line 1, "$(C_1-C_2)$alkyl" should be
-- $(C_1-C_{20})$alkyl --.
Claim 1, column 12, line 5, "$(C7-C_{11})$" should be -- $(C_7-C_{11})$ --.
Claim 1, column 12, line 7, "$(C_3-C_{12})$alkylene" should be
-- $(C_1-C_{12})$alkylene --.
Claim 4, column 12, line 16, "$(C_6-C4)$" should be -- $(C_6-C_{14})$ --.

Signed and Sealed this

Sixteenth Day of January, 1996

Attest:

BRUCE LEHMAN

*Attesting Officer*   *Commissioner of Patents and Trademarks*